United States Patent [19]

Sanchez et al.

[11] Patent Number: 4,976,865

[45] Date of Patent: Dec. 11, 1990

[54] METHOD FOR THE SEPARATION OF BIOLOGICAL MACROMOLECULES BY CHROMATOGRAPHY

[75] Inventors: Victor Sanchez, Ramonville Saint Agne; Beatrice Biscans, Escalquens; Jean-Pierre Couderc; Jean-Pierre Riba, both of Toulouse, all of France

[73] Assignee: Centre National de la Recherche Scientifique, Paris, France

[21] Appl. No.: 112,312

[22] Filed: Oct. 22, 1987

Related U.S. Application Data

[63] Continuation-in-part of Ser. No. 816,114, Jan. 3, 1986, abandoned.

[30] Foreign Application Priority Data

Jan. 4, 1985 [FR] France .................. 85 00643

[51] Int. Cl.$^5$ .......................... B01D 15/08
[52] U.S. Cl. ......................... 210/635; 210/656; 210/198.2; 426/422; 426/491; 426/583; 426/657; 530/366; 530/386; 530/413; 530/417
[58] Field of Search ............... 210/635, 656, 657, 658, 210/659; 426/422, 491, 583, 657; 530/413, 386, 417, 366

[56] References Cited

U.S. PATENT DOCUMENTS

| | | | |
|---|---|---|---|
| 2,959,542 | 11/1960 | Pye | 210/661 |
| 3,493,497 | 1/1970 | Pretorius | 210/656 |
| 3,522,172 | 7/1970 | Pretorius | 210/656 |
| 3,539,505 | 11/1970 | Lauer | 210/656 |
| 3,551,118 | 12/1970 | Cloete | 210/661 |
| 3,928,193 | 12/1975 | Melaja | 210/656 |
| 4,284,511 | 8/1981 | Weitzen | 210/661 |
| 4,443,231 | 4/1984 | Siegell | 55/100 |
| 4,675,113 | 6/1987 | Graves | 210/635 |

FOREIGN PATENT DOCUMENTS

| | | |
|---|---|---|
| 86068 | 1/1983 | European Pat. Off. . |
| 2638764 | 3/1977 | Fed. Rep. of Germany . |
| 2105032 | 9/1970 | France . |
| 2321932 | 8/1975 | France . |
| 2359634 | 7/1976 | France . |
| 1148661 | 4/1969 | United Kingdom . |
| 1422412 | 1/1976 | United Kingdom . |

OTHER PUBLICATIONS

Perry's Chemical Engineer's Handbook, Fourth Edition, McGraw Hill, N.Y., 1963, p. 4–25.
DeKoning, Gel Filtration, A New Method Applied for the Preparation of Milk, Neth. Milk and Dairy J. 16, 1962, pp. 210–215.
Curling, Methods of Plasma Protein Fractionation 1980, London, Academic Press, pp. 149–160.
Mirabel, Nouveau Procede de Valorisation de Lactoserum Information Chimie, No. 175, Mar. 1978, pp. 105–109.
Jones, Protein Recovery by Ion Exchange, Food Processing Industry, Apr. 1975, pp. 21–23.

*Primary Examiner*—Ernest G. Therkorn
*Attorney, Agent, or Firm*—Harold H. Dutton, Jr.

[57] ABSTRACT

A method for allowing biological macromolecules contained in a solution to be separated by selective absorption comprising supplying with a solution each stage (3, 4) of a column containing a selective chromatographic resin specific to the macromolecules to be separated, so as to fluidize the beds of resin at each stage, each stage being provided at its base with a perforated distribution system (5) characterized by a percentage of open sections between 0.2% and 10%, a mean diameter of the said open sections greater than approximately 300 microns and between $2G_m$ and $20G_m$, where $G_m$ is the mean granulometry of the resin.

11 Claims, 8 Drawing Sheets

METHOD FOR THE SEPARATION OF BIOLOGICAL MACROMOLECULES BY CHROMATOGRAPHY

CROSS-REFERENCE TO RELATED APPLICATION

This application is a continuation-in-part of copending application Ser. No. 816,114 filed Jan. 3, 1986, now abandoned.

This invention relates to a method and apparatus allowing biological macromolecules such as proteins, enzymes, toxins, antibodies, etc. to be separated by chromography, i.e. a process of adsorption, the prime characteristic of which is its selectivity, in order to obtain solutions enriched in one or more of the desired macromolecules.

BACKGROUND AND OBJECTS OF THE INVENTION

1. Field of the Invention

Certain biological molecules, known as biological macromolecules, are characterized by high molecular masses (greater than 5000) and a tendency to auto-denaturation leading to a loss of biological activity or functional capacity (e.g. denaturation of proteins into peptides); these properties limit the separation methods applicable for industrial purification (precipitation, ultrafiltration and chromatography). Chromatography methods (selective adsorption) constitute the most specific and best adapted preparation techniques currently available for industrial production of biological macromolecules at high degrees of purity.

These methods comprise percolating a solution containing the biological macromolecules through a fixed bed of specific chromatographic resins suitable for leading to their selective adsorption. In the event of the desired macromolecule(s) being fixed to the resin, the elution of the latter with a solution of appropriate pH or ion charge allows it or them to be separated and collected in a purified and concentrated form. If the desired macromolecule remains in the treated solution (the other macromolecules being fixed to the resin) then the desired separation is obtained directly.

2. Description of Related Art

This fixed-bed chromatography technique and its results are well known in the bio-technology field and study of the following documents provides excellent examples:

"Method of Plasma Protein Fractionation", by J. M. CURLING, Academic Press, 1980 p. 149–160, "Protein recovery by Ion Exchange", by D. T. JONES Bsc, Food Processing Industry, April 1975 P. 21, 23, "New Methods of Valorization of Whey": by B. MIRABEL, Rhone-Poulenc Industries, "Information chimie" (Chemical News) n 175, March 1978 p. 105–109, Patents FR No. 2.321.932 and 2.359.634 describing new ion-exchanging resins for protein separation.

However, these fixed-bed chromatography separation methods present some drawbacks, the most serious of which is the gradual clogging of the bed; this clogging is caused essentially by solid impurities in suspension in the solution and, often, by the precipitation of certain molecules of the solution itself.

The consequences are extremely serious from an industrial point of view. To maintain a constant flow of percolation over time the entry pressure of the solution must increase up to values in the order of 3 to 4 times greater than the nominal values which causes considerable technical difficulties and can even be unacceptable for certain applications. Furthermore, the cyclic cleaning of chromatographic resins is an extremely delicate operation in practice and generally necessitates cleaning in separate tanks, which prevents continuous operation of the equipment and imposes delicate and costly handling. It is to be noted that certain chromatographic resins, generally of a mineral nature, have fragile mediums which decompose during cleaning to give small particles which are subsequently likely to block certain zones of the bed and that other chromatographic resins, generally of an organic nature, cannot be cleaned when their meshes are blocked and so must be discarded. In certain cases, the blocking causes an integral saturation of the bed and cleaning is no longer possible. Another severe disadvantage of clogging is the change in fixation capacity of the resin bed after several cleanings: whatever precautions are taken a certain proportion of impurities remain fixed to the chromatographic resin and, little by little, its fixation capacity decreases until it becomes necessary to discard it.

These difficulties are well know to biological chromatography specialists and, in most cases, they necessitate a high degree of purification of the solutions before treatment. This purification greatly increases the cost of the method and limits its application for the production of high cost products (for example medicines ...)preventing its use in a great number of applications where the macromolecules produced have a lower value (treatment of certain natural products of a biological origin or by-products of industry especially the agricultural industry).

Another disadvantage of fixed-bed chromatography methods is the short life cycle of the resins which are rapidly destroyed by the constraints caused by their compression and the diverse intermediate cleaning and declogging treatments they undergo.

Currently, the problems mentioned above remain answered or unanswered at the price of a great increase in operating costs in the case of biological macromolecules; taking into account the economic importance of this type of treatment which affects not only the food sector but also the pharmaceutical sector, the veterinary sector, etc. . . . , several studies have been carried out to attempt to minimize the disadvantageous consequences summarized above in order to take maximum advantage of the performance of chromatographic methods for the separation of biological macromolecules. In this way certain writers have recommended the operation of a mobile compressed bed composed of a bed which is moved layer by layer by the removal of the resin at one extremity with its reinjection at the other extremity after cleaning (D. T. Jones BSc, "Protein Recovery by Ion Exchange"). However, no satisfactory solution for general application has so far been found, with certain serious disadvantages still existing such as for example, the need for cleaning, the deterioration of the fixation capacity and the wear of the chromatographic resins.

Besides, in other technical sectors, and in particular that of mineral separation, fluidized bed chromatography has long been carried out which avoids clogging and reduces the wear of the resins:

separation of metallic ions: "A Continuous Ion Exchange Column", by Turner and Church, *Trans. Inst. Chem. Engrs*, Vol 41, 1963 P. 283-288", uranium extraction: "Assessment of Fluidized Bed Ion Exchange Equipment", Michael J. Slater, *J. Appl. Chem. Biotechnol.*, 1975, vol. 25 p. 367-378".

These fluidized bed chromatography methods have been used for more than 20 years for the separation of molecules of small size (having good stability). However, biotechnicians have never tried to use them for biological macromolecule chromatography, because this technique has always appeared impossible to adapt to this type of treatment for various more or less objective reasons. Some relate, for specialists to the type of specific chromatographic resin for biological macro-molecules (too small granulometry, density too close to that of water, unacceptable physical nature), which would be impossible to fluidize without drawing particles into the flux. Another reason concerns the kinetics of fixation of biological macromolecules which, mainly due to the large space between molecules, would be subject to a decrease of efficiency in a fluidized bed making the method inoperable. Another reservation concerns the infinitely small speed at which it would be necessary to draw the solution through a fluidized layer (not possible for industrial production).

So, already in 1980, the existing bias was sufficiently anchored in the mind of the specialists for an eminent biotechnician to write in an aforementioned publication "Methods of Plasma Protein Fractionation", J. M. Curling, p. 152":

"We have decided on a fixed-bed column rather than a fluidized bed column. Fluidization imposes a rising filtration flow and large rather than dense particles in order to maintain an equilibrium against the rising forces. But the available gels for protein fractioning are rarely denser than water and would give extremely diluted suspensions even at very weak flow speeds. In addition, because of the flow dispersion of macromolecules, the particle size and the inter-particle volumes should be as small as possible in order to increase the probability of the liquid element penetrating the porous internal volume. A fixed bed results in a minimal column volume and economizes on water consumption. All these arguments have not negligible financial consequences when choosing a general method. With all these requirements, it is evident that the exploitation of chromatography in the bio-industrial sector requires special apparatus having exceptional mechanical qualities. It must be possible to sterilize them when used in as compact a column as possible and to use as high a flow speed as possible for the daily treatment of several hundreds or thousands of liters of solution."

It must be noted that two earlier patents (GB patent No. 1.148.661 dated 09.05.66 and FR patent No. 2.105.032 dated 17/09/70) mention, in the case of one fixed-bed fluidized or open column chromatography for biological molecules, or for the other an ion exchange in a fluidized bed to purify hard water or uranium salts giving as a potential application the purification of biological substances. however, it is understandable that these patents were not able to prevent the bias, mentioned above, from forming. In fact, the former patent which envisages treatment in turbulent conditions, whether the bed be fixed fluidized or open, simply describes two examples of biological molecule chromatography both concerning small-sized molecules: codeine and atropin; besides this, in the general section, reference is made in this patent to a list of potential applications: hormones, vitamins, alkaloids, antibiotics, which are all small molecules apart from certain hormones. The second patent provides solely the examples of hard water purification to remove salts and of a uranium sale purification; this patent mentions in the general introduction, the application of the ion exchange process to biological substances and it is known that simple ion exchange processes are not applicable to small-sized molecules (contrary to the chromatography processes which involve selective chromatography resins of a specific type).

The present invention proposes an improvement of the current biological macromolecule chromatography separation technique in the biotechnology sector. It aims at the chromatography of molecules having a high molecular weight (greater than 5,000), such as proteins, enzymes, toxins, antibodies.

3. Objects

An essential objective of the present invention is to allow, in particular, the exploitation of chromatographic separation techniques avoiding the biggest drawback of these techniques, bed-clogging.

Another objective linked to the previous one is to reduce considerably the wear of the resin particles making up the bed.

Another objective is to authorize a continuous use of the separation techniques.

Another objective is to make biological macromolecule chromatographic separation feasible economically on an industrial scale for large numbers of particles of high-molecular weight, particularly to ensure the valorization of either agro-food industry protein by-products, or natural products such as milk, blood, plasma, or blood serum, or synthetic products.

DESCRIPTION OF THE INVENTION

Figure 1:
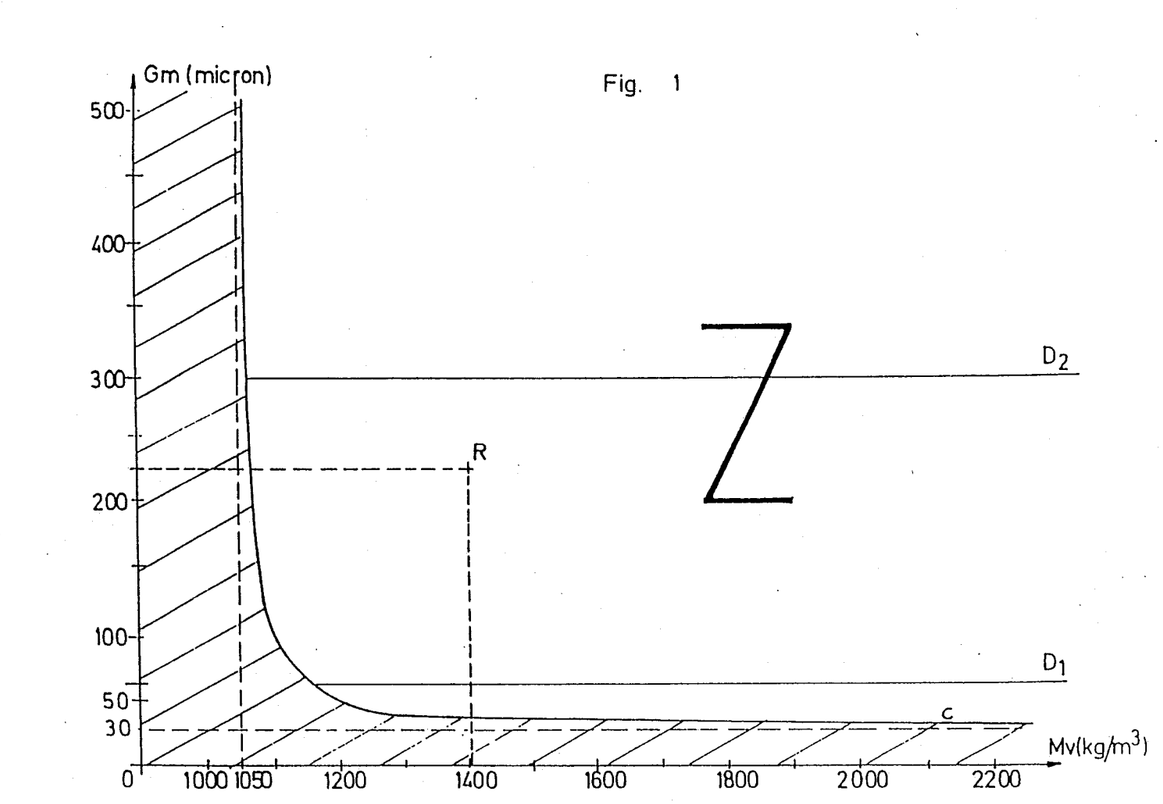
FIG. 1 already mentioned is a diagram giving the specifications of appropriate resins.

To this end, the method subject of the present invention for carrying out the chromatographic separation of biological macromolecules contained in the solution comprises bringing the solution into contact with a bed of selective chromatographic resins, specific to the macromolecules to be separated in order to carry out a selective adsorption; according to the present invention, the method may be characterized thus:

A chromatographic resin is used having a mean granulometry ($G_m$) and a density (D) of values located within zone Z which is the non-hatched area of the diagram of FIG. 1;

The said chromatographic resin is placed in a column of at least one stage provided at its base with a perforated distribution system of the following characteristics:

percentage of open sections approximately between 0.02% and 10%, mean diameter of open sections greater than approximately 300 microns, mean diameter of open sections between approximately 2 $G_m$ and 20 $G_m$, Each stage of the column is supplied via its distribution system with the solution so as to fluidize the chromatographic resin bed, by adjusting the flow of the solution to obtain a linear speed of the liquid (corrected for the total straight section) comprised approximately between 1.5 $V_{mf}$ and 12 $V_{mf}$, where $V_{mf}$ is the minimum speed of fluidization of the resin.

The mean granulometry (G) of the resin is usually defined by the formula $$G_m = \frac{\Sigma xi\, Gi}{\Sigma xi}$$

where xi is the mass of the fraction of particles having a granulometry Gi.

So, in a way unexpected according to the findings of the prior state of the art, it has been observed that it is possible to carry out chromatographic separation of macromolecules, by selective adsorption in a fluidized bed, by combining aforementioned conditions relating to the chromatographic resin and the distribution of the solution (structure of the distributors, supply flow). Surprisingly, as the following examples will show, use of a fluidized bed does not reduce the exchange capacity of the chromatographic resin and the selective transference remains in all respects essentially similar to those obtained with a fixed bed.

In the preferred embodiment the chromatographic resin will have a mean granulometry ($G_m$) between 75 and 300 microns corresponding to the horizontal band between the limit curve C and the two straight lines $D_1$ and $D_2$ on the diagram of FIG. 1. It turned out that the scatter of grain size should not be too great and that a prior sifting of the said resins should preferably be carried out in order to limit scatter to about 50% either side of the mean $G_m$.

Furthermore, following a preferred embodiment, the chromatographic resin is placed in an essentially vertical column composed of between 2 and 5 stages placed on top of the other, which the solution successively passes through, the said solution being drawn off by an overflow on the upper part of the upper stage, each stage (with the exception of the uppermost one) being separated by two perforated distribution systems, one distributing the solution at the base of the stage in question, the other distributing the solution towards the stage located immediately above.

It has been observed that, for a global quantity of chromatographic resin, fluid bed fractioning at several levels greatly increases separation performance in a given time and allows results comparable to those of a fixed-bed. This phenomenon may be explained by the fact that a concentration gradient (favoring separation), which exists naturally in a fixed-bed but not in a single-stage fluidized bed, tends to be recreated.

In this way, the method of the invention allows fixed-bed performance figures to be practically reached, as well as avoiding the serious disadvantages of this type of bed: clogging, need for cleaning, compression and cleaning-induced resin deterioration. In fact, the fluidized bed allows free passage of impurities in the solution with no risk of clogging; no cleaning is necessary so the life-span of the resins is greatly increased.

Furthermore, the method allows continuous exploitation as the constraints imposed by cleaning do not exist: the chromatographic resin can circulate perpetually from top to bottom in the column, with a continuous resin supply at the top part and a continuous drawing off at the bottom part fluidized bed separation occurring continuously in the column, with the concomitant execution of washing and elution operations outside the column.

Confusion must be avoided between conventional washing operations which comprise a simple rinsing using distilled water or other solution; or an elution operation which comprises the passage of a regeneration solution, with the cleaning or de-clogging operations, requiring in the known methods an energetic mechanical treatment of the resins which are at the origin of their deterioration and difficulties for a continuous operation.

Chromatographic resin circulation between two superimposed levels may be ensured by a tube, disposed so as to allow the resin to circulate by overflow into the said tube of the upper level to the lower level.

Furthermore, in a preferred embodiment one or more baffles should be installed at each level to ensure the complete circulation of resin in each level, without the fluid stagnating.

Of course, the invention method may, if required, allow continuous operation: in this case the chromatographic resin is enclosed within each stage in the absence of circulation from one stage to another, the fluidized bed separation being carried out by cycles of selective fixation, washing, elution and washing in the column. This mode of exploitation remains advantageous in relation to fixed bed separation for the reason already mentioned: in particular, it is not necessary to dismantle the column for de-clogging.

In the two operation cases (continuous, discontinuous) the column is sufficiently supplied so that the internal solution flow remains essentially constant throughout the selective fixation phases, the variation of this flow in relation to its nominal value being less than ±5%.

This arrangement guarantees stable fluidization of the chromatographic resin without risk o accidental grain induction.

The invention method is generally applicable for the separation of all biological macromolecules; for each application trained personnel are capable of choosing a chromatographic resin (voluminal mass and granulometry conditions provided by the diagram of FIG. 1) and to create a perforated distribution system suitable for the granulometry of the said resin (open section diameter conditions already mentioned).

In particular, the invention method may be applied to the chromatographic separation of whey proteins; the resins used may notably be of the "Spherosil resin" type, commercialized under this name by "Rhone-Poulenc" Company and described in French patent No. 2.321.932; this resin meets the specifications given in the diagram of FIG. 1.

BRIEF DESCRIPTION OF THE DRAWINGS

The following description gives a non-exhaustive list of some examples of exploitation of the method, in some cases in a discontinuous installation (Examples 1 and 2), in another, a continuous installation (Example 3); the diagrams included in the annex represent these installations.

DESCRIPTION OF PREFERRED EMBODIMENTS

Figure 2:
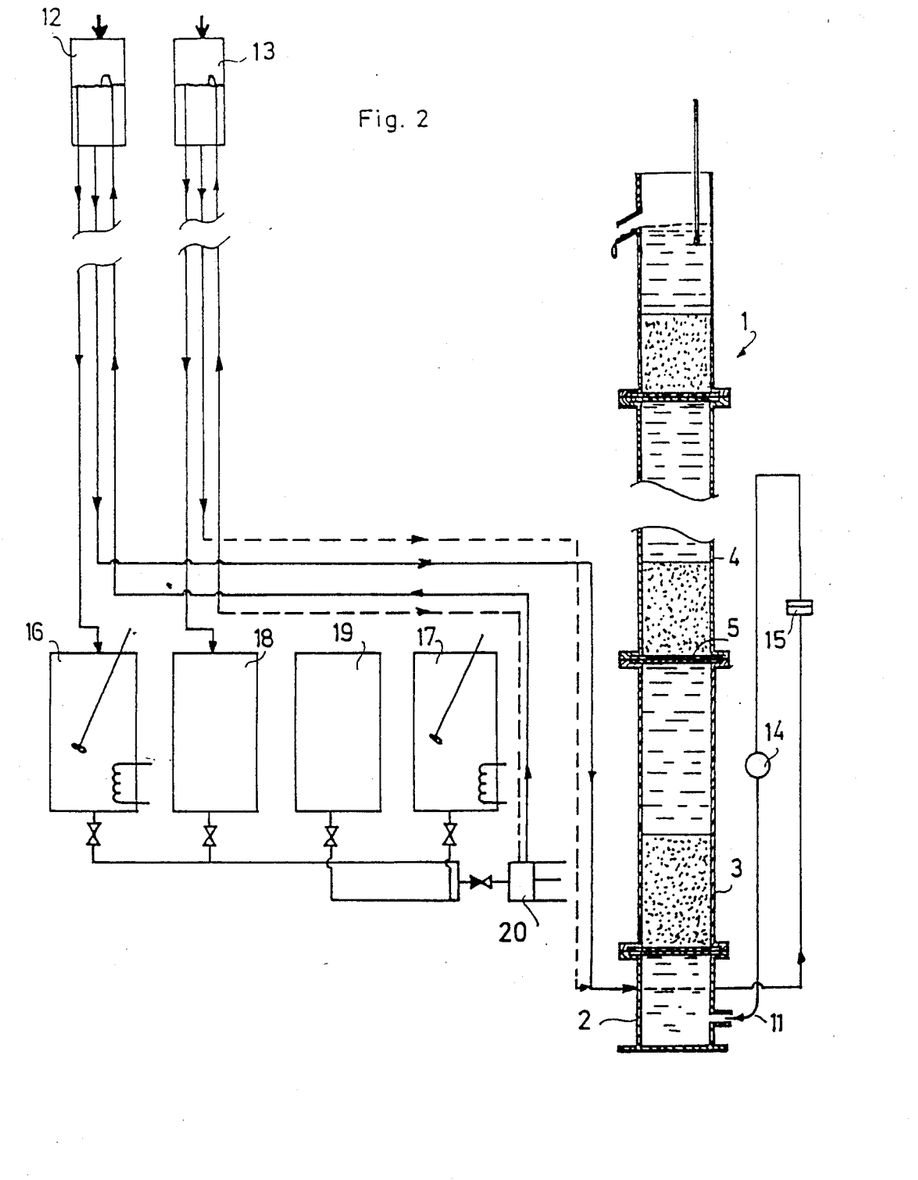
FIG. 2 is a plan view of a discontinuous installation for exploitation of the method.
Figure 3:
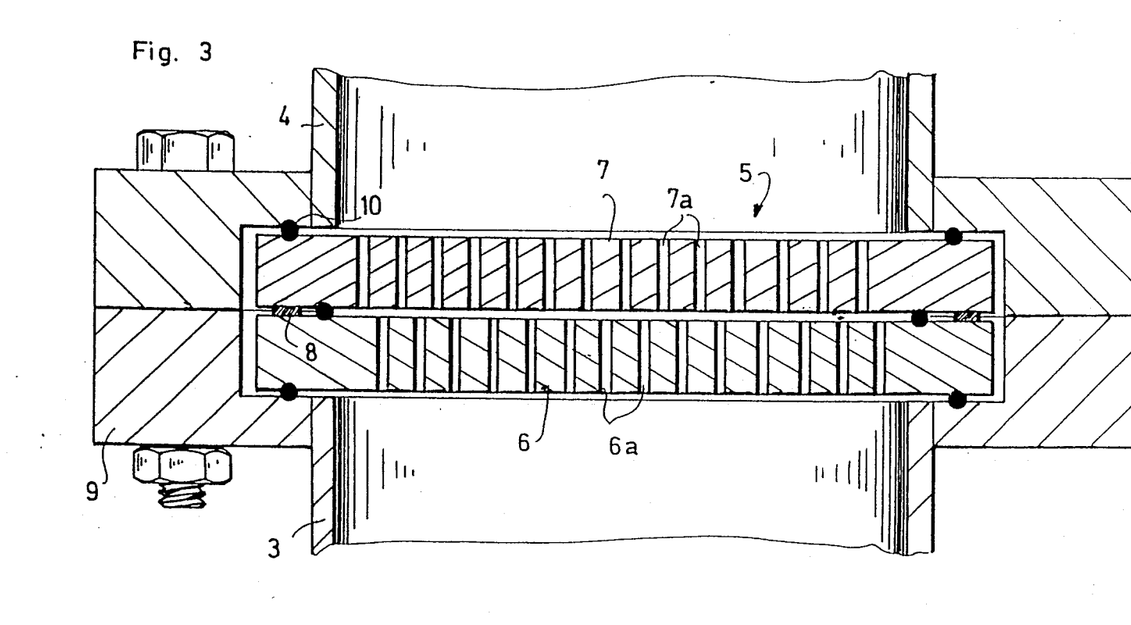
FIG. 3 is a detail view of a vertical section of the column of the installation of FIG. 2

The installation shown for explanation purposes in FIGS. 2 and 3 is intended to ensure a chromatographic separation of biological macromolecules according to a cyclic operation process, alternating between a fixation phase, a washing phase, an elution phase and another washing phase.

Throughout these different phases, the specific chromatographic resin in enclosed in a vertical column (1) of several stages, such as (3) and (4). Three or four stages could be envisaged in practice.

The column (1) includes a base (2) which allows the distribution of the solution to the lower stage (3) through a perforated distribution system. This system is identical for all stages and has been represented as (5) at the expanded scale of FIG. 3.

It comprises two perforated cylindrical plates (6) and (7) (or, if desired, a greater number of plates) which are placed one on top of the other, with a space between each plate being maintained by shims (8).

Plates (6) and (7) are provided with perforations (6a) and (7a) and are positioned so that the perforations of one plate are off-set from those of the adjacent plate.

The distribution density of the plates is such that the percentage of open sections comprises between 0.02% and 10% and, in particular, equal to 5% in the examples described below. By percentage of open sections is usually understood the ratio in a given straight section of the sum of open surfaces to the useable surface of the plate.

In addition, the perforations of each plate are designed so that each as a diameter greater than 300 microns. Above this limit the diameter of the perforations is adapted to the mean granulometry $G_m$ of the resin employed; a value in the order of 4 $G_m$ to 6 $G_m$ would seem to give the best results. For example, for the "Spherosil" resins in the examples, a plate was used having perforations with a diameter of 1 mm.

Plates (6) and (7) are maintained at their circumference by bolted annular flanges (9). The cylindrical elements (3) or (4) or base (2) ar bonded at the periphery to the internal annular surfaces of the flanges. Also, 0-rings such as (10) ensure peripheral sealing between plates and between plates and flanges.

The solution (solution to be treated during the fixation phase, distilled water solution during the washing phases or regeneration solution during the elusion phase) enters the base (2) via a tube (11). To maintain the flow strictly constant, these solutions are placed in reservoirs (12) (treated solution or regeneration solution) and (13) (distilled water solution) which are placed at an appropriate height above the column (1) to deliver the desired flow. A flowmeter (14) and a diaphragm (15) allow this flow to be precisely regulated.

The solution to treat is stored in a tank (16) where it is shaken and maintained at a regulated temperature. The regeneration solution is stored under the same conditions in a tank (17). The distilled water is stored in a tank (18). The solution leaving the column may be stored in a tank (19). A pump (20) and a system of tubes and valves allows reservoirs (12) and (13) to be supplied during each phase with the appropriate solutions from tanks (16-18) so that the level of the reservoirs remains essentially constant.

The system described above ensures supply to the column (1) with a flow whose variations are in practice lower than ±5%.

At the outlet of the column (1), the liquid is collected by overflow at the upper part of the upper stage to be finally stored in the tank (19).

Figure 4:
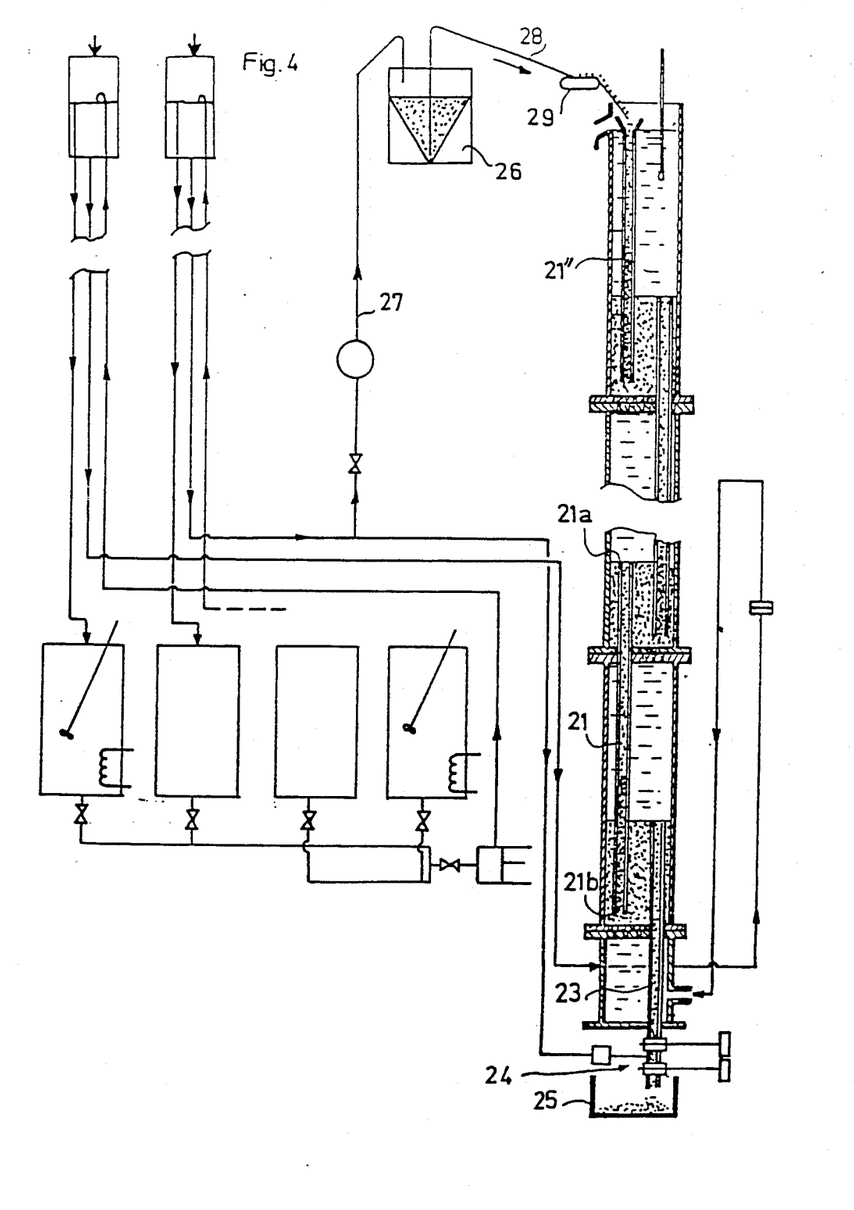
FIG. 4 is a plan view of a continuous installation.

Furthermore, FIG. 4 shows a plan for an installation modified in relation to the previous one in order to provide continuous operation. The column, its perforated distribution systems and the means of ensuring a constant flow of liquid supply are similar.

However, in this installation, the chromatographic resin is made to circulate continuously from one stage to the lower stage and the washing and elution phases are carried out outside the column, the latter performing the continuous chromatographic fixation cycle.

Figure 5:
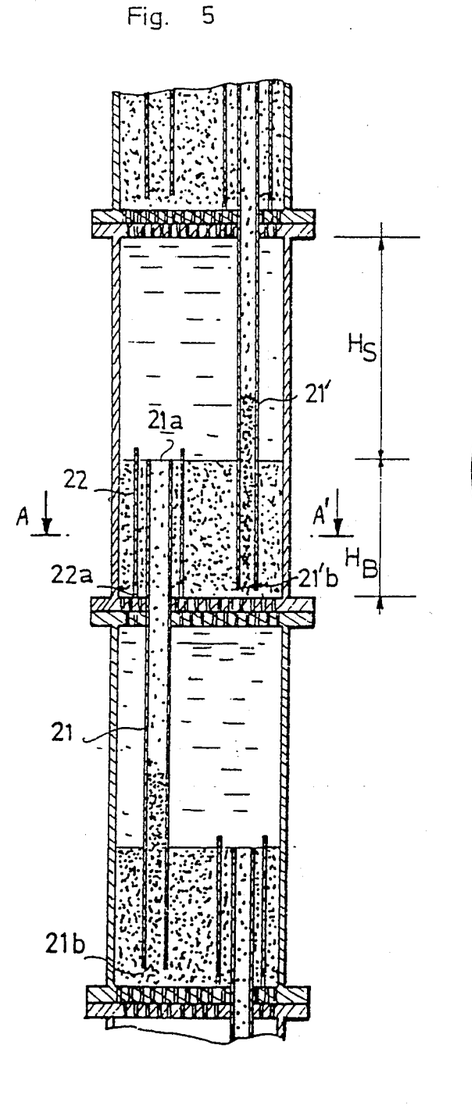
FIG. 5 is a detail view of a vertical sectional view of the column of the said installation.
Figure 6:
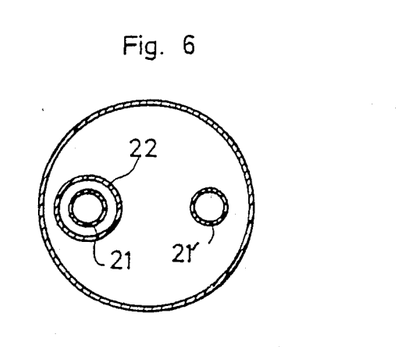
FIG. 6 is a cross sectional view along a horizontal plane AA'.

The modifications to the installation are as follows:

As shown in FIG. 5, between two superimposed stages on the column, a resin transit tube (21) is installed which crosses the perforated distribution system. This tube extends between the upper part (21a) of the bed of the upper stage and the lower part (21′b) of the bed of the lower stage. Thus the resin is free to circulate by overflow in the various tubes (21), successively from one stage to the lower one.

To ensure this overflow, each transit tube (21) is higher, at each stage, by a height $H_B$ less than the height $H_S$ of the non-occupied portion of the stage in question. Thus, the fluidized resin bed which is formed within each tube (21) does not overflow from the tube to the stage above, which constitutes the condition for circulation by gravity of the resin from one stage to the lower stage.

Furthermore, at each stage a baffle (22) is installed between the two apertures of the two tubes (21) which flow into the stage in question (lower aperture (21b) of the tube leading to the upper stage and the upper opening (21a) of the tube leading to the lower stage). Each baffle (22) may be made up of a tubular sleeve around the tube (21); this sleeve extends at its upper part above the level of aperture (21a) and maintains at it slower part a passage (22a) for the resin.

The resin coming from the upper stage and flowing from aperture (21′b) is less concentrated and so generally lighter and tends to rise in the bed; baffle (22) prevents the creation of a short-circuit of the resin between the apertures (21′b) and (21a): it avoids stagnant zones in the bed where the resin would not be renewed and thus ensures that the latter is entirely renewed (it should be noted that for certain resins and certain macromolecules to be fixed, the voluminal mass of the resin does not alter during the exchange; in this case, the baffle is less indispensable but improves the overall fixation uniformity).

Moreover, at the lower part of the column, the inner transit tube (23) passes through the supply base and is with hydraulic resin drawing means (24) to, in the example, a recovery tank (25). The resin in this tank is regenerated in an outer column, which can also operate as a fluidized bed; drawing towards this outer column may be assured continuously.

The regenerated chromatographic resin is dispatched to a storage tank (26) either by continuous transfer from the regeneration column or by manual supply. This hermetically sealed tank is filled with distilled water and may be supplied with distilled water by a duct (27) provided with a valve and a flowmeter.

The resin may be hydraulically conveyed through a tube (28) to a conveyor belt (29) combined with a vacuum pump in order to eliminate the moisture around the grains of resin.

The conveyor belt (29) deposits the regenerated resin at an adjustable rate in an upper transit tube (21') and provided with an upper funnel.

Examples 1 and 2 have been embodies on an installation of the type shown in FIG. 2 and Example 3 on an installation of the type shown in FIGS. 4 and 5.

EXAMPLE 1

The column of the installation comprises three stages in this example; the height of each stage is 50 cm, the diameter of the column 5 cm.

This example is intended to extract $\beta$-lactoglobulin (molecular mass in dimeric form: 34,000) and $\alpha$-lactalbumin (14,000) albumins of a mild whey, cheesemaking residue provided by "Bel" cheesemakers.

The chromatographic resin used is "Spherosil QMA" resin manufactured by "Rhone-Poulenc".

The initial granulometric scatter is from 100 to 300 $\mu$m. A dry sifting retains grains in the range 200–250 m, i.e. a mean granulometry of $G_m = 225$ m. The voluminal mass of the "Spherosil QMA" resin is $M_v = 1,400$ kg/m$^3$. The couple of values ($G_m$, $M_v$) characterizing the said resin is shown on point R on the diagram in FIG. 1.

This resin is a chromatographic resin comprising Silicium spheric grains with a specific surface of 25 m$^2$/g, a mean porous diameter of 1 cm$^3$/g, covered with a reticulated polymer Styrene Vynil Triethoxsilane, with the following functional groupings:

The minimum fluidization rate of such a resin is $V_{mf} = 1.4 \times 10^{-4}$ m/s.

The average diameter of the open sections of the distributor at each stage of the column corresponds, in these conditions, to approximately: 4 $G_m$.

The quantity of resin deposited at each stage is 130 cm$^3$.

The column is supplied with whey at its base at a solution flow of 9 l/h not varying more than 5% with respect to this nominal value due to the nature of the supply means planned (loaded tanks with determined height).

This flow in a column with a $1.96 \times 10^{-3}$ m$^2$ cross section corresponds to a fluid rate of $1.3 \times 10^{-3}$ m/s, i.e. 9 $V_{mf}$.

When the flow is established, an expansion of 64% and a height of 20 cm is observed in the bed on each stage. A proper, stable fluidization can be seen.

At its inlet, the whey has the following concentrations: 3.0 g/l in $\beta$-lactoglobulin and 1.2 g/l in $\alpha$-lactalbumin.

Figure 7:
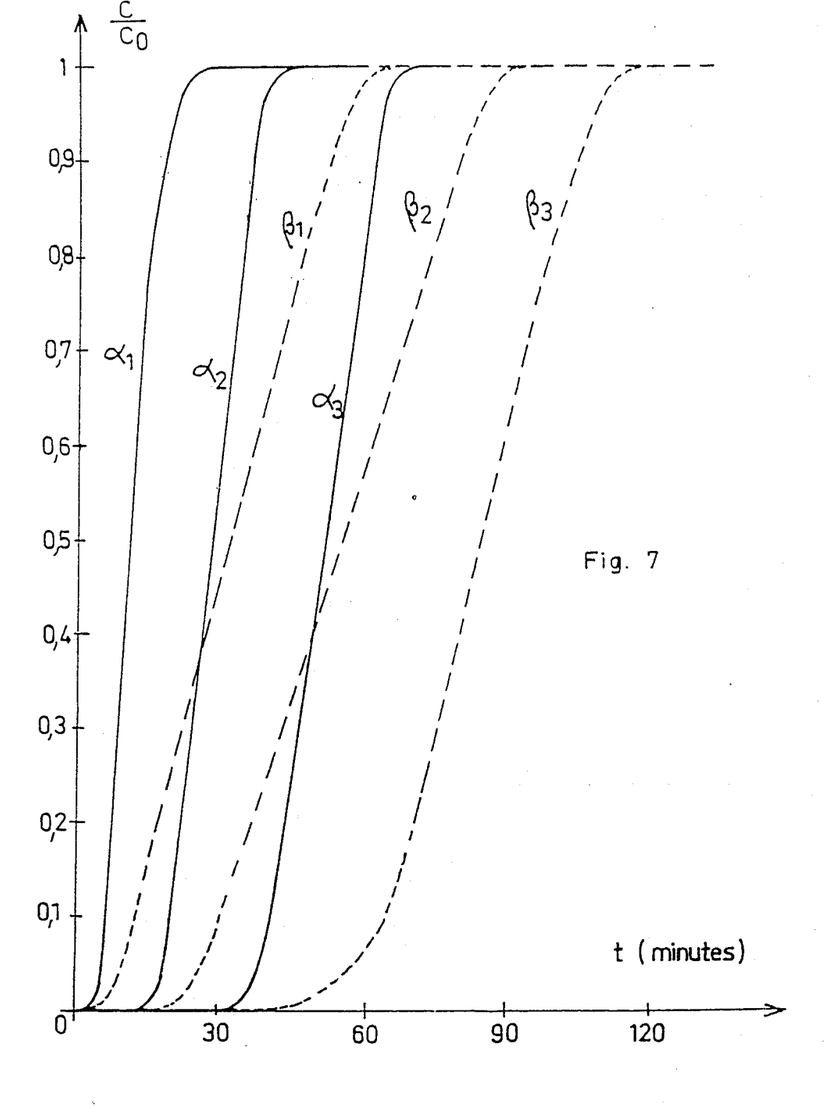
FIGS. 7, 8, and 9 are diagrams showing, as a function of time, the change in concentrations of the final solutions for each of the Examples 1-3 respectively.

The process operates for two hours. FIG. 7 shows the curves providing the ratio of the concentration at the outlet of each stage C to the initial concentration Co, as a function of time; curves $\alpha_1$, $\alpha_2$, and $\alpha_3$ represent the variation C/Co for a $\alpha$-lactalbumin, at the outlet of the lower, intermediate and upper stages, respectively. Curves $\beta_1$, $\beta_2$, and $\beta_3$ represent the variation C/Co for $\beta$-lactoglobulin at the outlet of the lower, intermediate and upper stages, respectively. The measurements are performed on samples taken every 3 minutes, by zone electrophoresis on a cellulose acetate membrane.

For 30 minutes the $\beta$-lactoglobulin and the $\alpha$-lactalbumin are observed to be entirely fixed on the resin (initial plateau phase of curves $\alpha_3$ and $\beta_3$), then only the $\beta$-lactoglobulin continues to be absorbed about fifteen minutes more, while the $\alpha$-lactalbumin is in the outlet current in the column.

When the fixing operation is over (C/Co=1), washing with distilled water is carried out for approximately 20 minutes.

The resin is then eluted with a 0.1 N Hydrochloric acid solution for two hours.

Another washing with distilled water is then carried out for approximately an hour and the column is then ready for another cycle. During all these operations (washing, elution) the resin in the column is fluidized in a similar manner.

The quantity of proteins from the elution phase is 10.5 g for the $\beta$-lactoglobulin which corresponds to a fixation of 102 mg per gram of dry resin and 1.7 g for the $\alpha$-lactalbumin which corresponds to 16.5 mg per gram of dry resin. So the evaluate contains 86.1% of $\beta$-lactoglobulin and 13.9% of $\alpha$-lactalbumin. Now, the relative proportions of these proteins in the initial product (whey) were 71% $\beta$-lactoglobulin and 29% $\alpha$-lactalbumin. So there is an enrichment in $\beta$-lactoglobulin.

The elution containing these proteins is freed of lactose, casein and mineral salts initially contained in the whey, as the proteins are pure and in their native (undenatured) state.

The fixing capabilities of "Spherosil QMA" resin in a three-stage fluidized layer are essentially identical to those obtained with a fixed layer during prior work, of the following publications:

SKUDDER, P. J. "Recovery and Fractionation of Proteins from Cheese Whey Using a Porous Silica-Based Ion Exchange Medium", *Chemistry and Industry*, 21, 810–814 (1983).

BOURGEOIS C. M. and LEROUX, P. "Animal Proteins (Concentrated Extracts and Isolates in Human Food)", Chap. 3, *Collection Sciences Techniques Agroalimentaires*, Lavoisier (DR).

The tests described above have been renewed dozens of times without any clogging being observed either in the layer or the distributors; it should be noted that the whey used was in its raw state and contained solid impurities in suspension.

Moreover, no drop in the efficiency of the resin or wear of the latter was observed.

EXAMPLE 2

This example is embodied in the same conditions as Example 1, except for the quantity of resin deposited on each stage, which is 110 cm$^3$.

When the flow is established, an expansion of 69% and a height of 18 cm is observed in the bed on each stage. A proper, stable fluidization can be seen.

At its inlet, the whey has the same characteristics as in Example 1 (3.0 g/l in $\beta$-lactoglobulin and 1.2 g/l in $\alpha$-lactalbumin).

Figure 8:
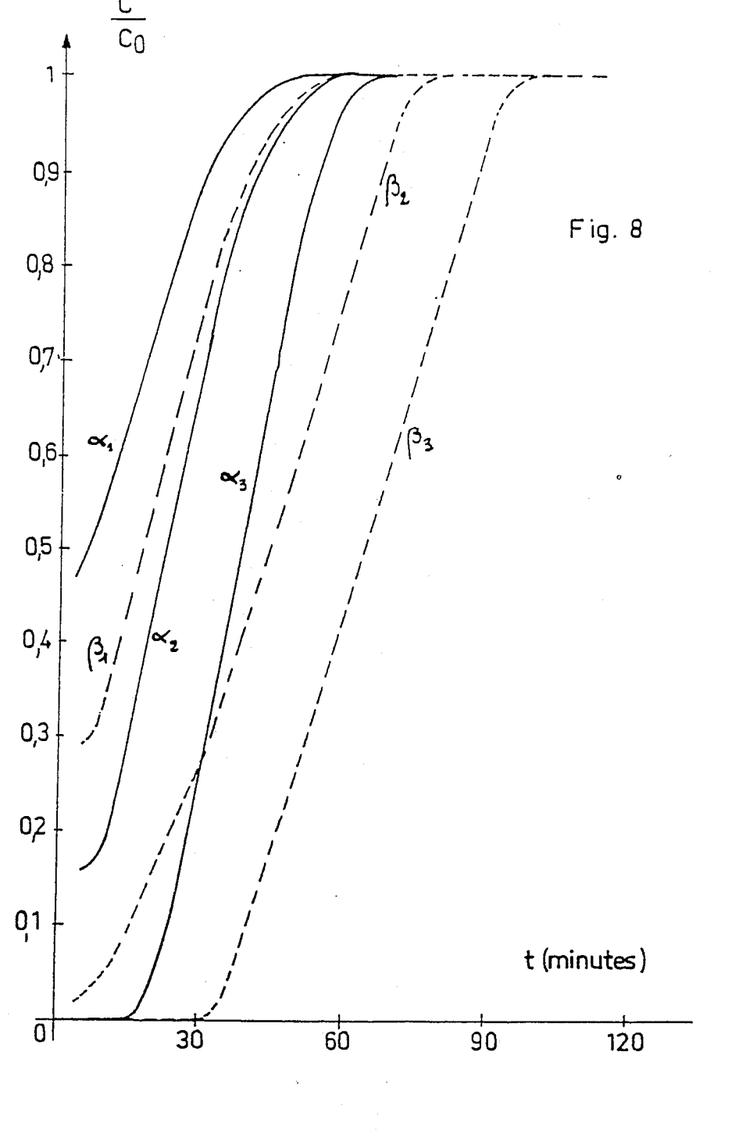

The process operates for two hours. FIG. 8 shows the curves providing the ratio of the concentration at the outlet of each stage C to the initial concentration Co.

The concentration of resin on each stage is seen to be less dense than in Example 1, the duration during which both proteins, on one hand, then only the β-lactoglobulin, on the other, are absorbed is shorter than in Example 1 (by about 15 minutes each).

The process of washing, elution, washing is the same as in Example 1.

The quantity of proteins obtained by elution corresponds to a fixation of 110 mg per gram of dry resin for the β-lactoglobulin and 19.5 mg per gram of dry resin for the α-lactalbumin. So, the eluate contains 84.9% of β-lactoglobulin and 15.1% of α-lactalbumin. Taking experimental and analytic errors into account, these proportions are analogous to those observed in Example 1.

EXAMPLE 3

This example has been embodied in the installation described above and illustrated in FIGS. 4 and 5, the column comprising three stages 60.5 cm high each.

This example is intended to extract β-lactoglobulin and α-lactalbumin albumins from a mild cheesemaking residue whey provided by "Bel" Cheesemakers.

The resin used ("Spherosil QMA") has the same characteristics as in Example 1.

The mean diameter of the open sections of the distributor at each stage on the column is 4 $G_m$.

The junction tubes used to convey the resin from the top to the bottom of the column has an internal diameter of 1.4 cm and exceed each stage by a height of $H_B = 25$ cm.

The flow of the resin inserted in the column is maintained at 0.14 l/h.

The resin drain system at the base of the column comprises three electromagnetic, timer-controlled valves. The solid particles transit via the open upper valve and accumulate in the plastic hose. Every 20 seconds, the upper valve is closed while the side valve opens at the same time as the lower valve injects distilled water which draws the particles toward the bottom.

The column is supplied at its base with whey at a solution flow of 9 l/h, this flow being controlled in the same manner as in Example 1.

When the flow is established, a height of 25 cm is observed in the bed on each stage, corresponding to the height the junction tube exceeds the stage in question.

Each stage has a height of 60.5 cm so that the height of the fluidized layer retained in the junction tube of the stage has a level lower than that in the fluidized layer on the stage immediately above, so preventing the resin from overflowing into the stage above.

A proper, stable fluidization and a proper circulation of both solid and liquid phases are observed.

At its inlet, the whey has the following concentrations: 3.0 g/l in β-lactoglobulin and 1.2 g/l in α-lactalbumin.

Figure 9:
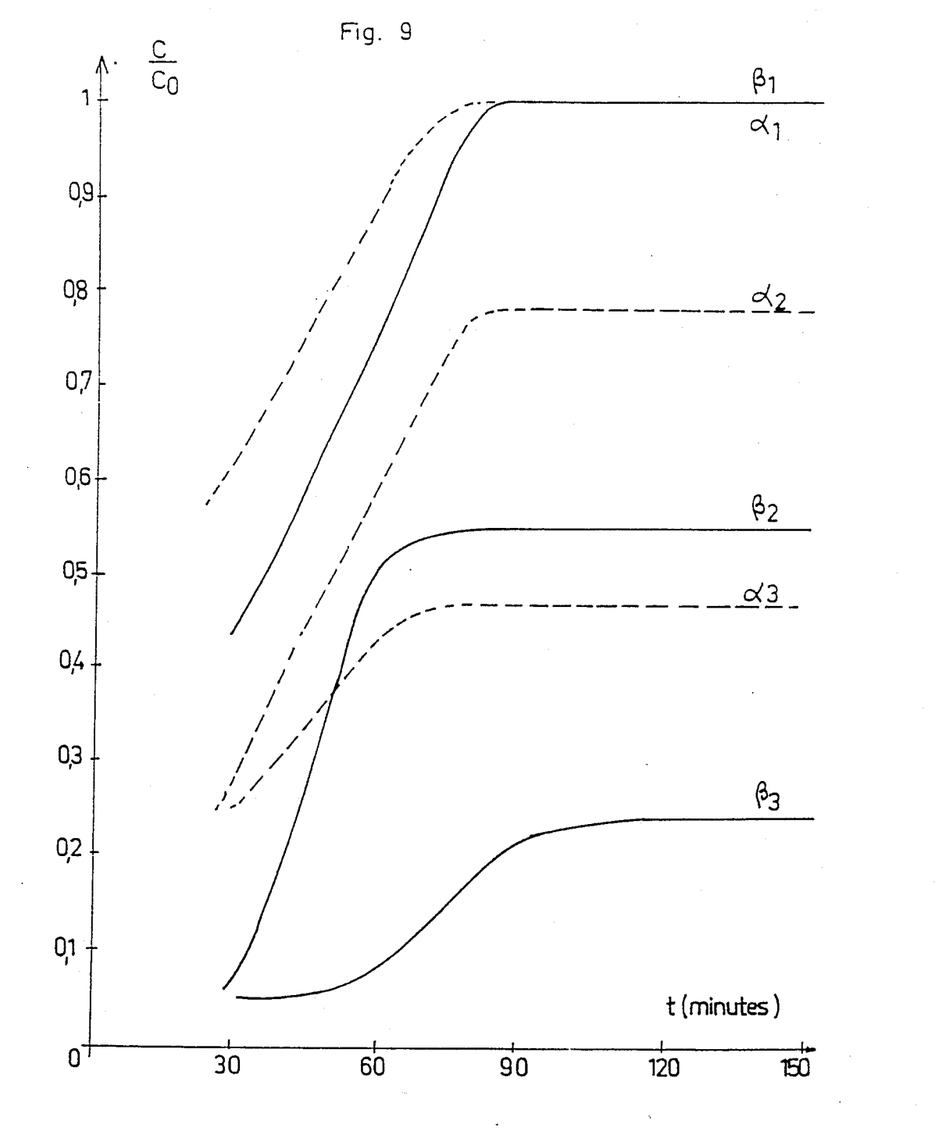

The process operates continuously but, in the example in question, operates for three hours. FIG. 9 illustrates the curves providing the ratio of the concentrations at the outlet of each stage C to the initial concentration Co.

The operation is seen to have a transient phase before reaching a stationary operating rate.

The α-lactalbumin ($\alpha_1$, $\alpha_2$, $\alpha_3$) is observed to be retained in lesser quantities on the resin than the β-lactoglobulin ($\beta_1$, $\beta_2$, $\beta_3$).

At the outlet of the column (third stage) the fluid contains approximately 50% of the initial α-lactalbumin while it contains no more than 25% of the β-lactoglobulin, the remainder having been fixed on the resin.

We claim:

1. A method for the chromatographic separation of biological macromolecules on an industrial scale having a molecular weight of greater than 5,000, having a tendency to autodenaturation, and selected from the group consisting of proteins, enzymes, toxins and anti-bodies in solution for performing a selective adsorption comprising providing a quantity of selective chromatographic resins specific to the macromolecules to be separated and having a mean granulometry $G_m$ and a voluminal mass $M_v$ so related as to fall within non-hatched Zone Z in the graph of FIG. 1; providing a chromatographic column with at least one stage having at its base a perforated distribution system with open sections between about 0.02% and 10%, said open sections having a mean diameter greater than about 300 microns and within the range of 2 $G_m$ and 20 $G_m$; placing said chromatographic resin in said chromatographic column so as to form a bed; supplying a flow of said solution through said distribution system to said chromatographic column in such a manner as to fluidize said bed and adjusting said flow so as to obtain a linear liquid speed in said column of between about 1.5 $V_{mf}$ and 12 $V_{mf}$, where $V_{mf}$ is the minimum fluidization speed of said resin.

2. A method as in claim 1 and including providing said column as a vertical column having between 2 and 5 superimposed of said stages, supplying said flow so as to pass successively through said stages, drawing off said solution by overflow at the uppermost of said stages, and providing each of said stages with two of said distribution systems whereby one of said distribution stages distributes said solution within said stage and the other of said distribution systems distributes said solution to the next superjacent stage.

3. A method as in claim 2 and wherein the chromatographic resin(s) in each of said stages is confined within said stage without circulation of resins(s) between stages, and wherein the separation is carried out by sequential cycles of fixation, washing, elution and washing in the column.

4. A method as in claim 2 and including causing said chromatographic resin(s) to circulate continuously in said column from top to bottom by continuously supplying said chromatographic resin at the top of said column and continuously drawing off said chromatographic resin at the bottom of said column, while carrying out said separation continuously and carrying out steps of washing, elution and washing of said resin(s) outside of said column.

5. A method as in claim 4 and including providing a resin transport tube between superimposed stages of said column, said transport tube passing through said distribution system and extending between the upper portion of the upper stage and the lower portion of the lower stage, thereby circulating said resin(s) from the upper stage to the lower stage by overflow.

6. A method as in claim 5 and including providing at least one baffle in the resin bed for separating said bed and assuring a complete renewal of the resin within the stage.

7. A method as in claim 6 and wherein said transport tube is mounted in said column in such a manner that the fluidized bed resin in a transport tube of one stage does not overflow from the tube into the stage above.

8. A method as in claim 1 and including supplying said flow of said solution so that the flow inside said column is substantially constant so as to have a variation in flow rate of less than about ±5%.

9. A method as in claim 1 and wherein said perforated distribution system comprises at least two spaced superimposed, perforated plates, said plates being so positioned with respect to each other that the perforations in one plate are off-set with respect to the perforations of the other plate.

10. A method as in claim 1 and including carrying out said method on a solution containing the proteins of a whey.

11. A method as in claim 10 and wherein said chromatographic resin comprises a spherosil type having a granulometry $G_m$ of about 75 to 300 microns pre-screened so as to have a particle size variation of at most 50%, and carrying out said method for the extraction of β-lactoglobulins and α-lactalbumins from a lactoserum.

* * * * *